United States Patent
Ostapoff et al.

(10) Patent No.: US 9,775,928 B2
(45) Date of Patent: Oct. 3, 2017

(54) ADHESIVE BARBED FILAMENT

(71) Applicant: Covidien LP, Mansfield, MA (US)

(72) Inventors: Roland Ostapoff, East Haven, CT (US); Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 516 days.

(21) Appl. No.: 14/269,225

(22) Filed: May 5, 2014

(65) Prior Publication Data

US 2014/0371767 A1    Dec. 18, 2014

Related U.S. Application Data

(60) Provisional application No. 61/836,374, filed on Jun. 18, 2013.

(51) Int. Cl.
| | | |
|---|---|---|
| A61B 17/06 | (2006.01) | |
| A61L 17/10 | (2006.01) | |
| A61B 17/00 | (2006.01) | |
| A61F 2/00 | (2006.01) | |
| A61B 17/072 | (2006.01) | |

(Continued)

(52) U.S. Cl.
CPC ...... *A61L 17/105* (2013.01); *A61B 17/00491* (2013.01); *A61B 17/06166* (2013.01); *A61L 17/10* (2013.01); *A61B 17/07292* (2013.01); *A61B 17/12131* (2013.01); *A61B 2017/00004* (2013.01); *A61B 2017/005* (2013.01); *A61B 2017/00495* (2013.01); *A61B 2017/00893* (2013.01); *A61B 2017/00951* (2013.01); *A61B 2017/0406* (2013.01); *A61B 2017/06057* (2013.01); *A61B 2017/06176* (2013.01); *A61B 2017/06185* (2013.01); *A61F 2/0063* (2013.01); *Y10T 29/49801* (2015.01)

(58) Field of Classification Search
CPC ........... A61B 2017/06057; A61B 2017/06185; A61B 2017/06176; A61B 17/06166
USPC .......................... 606/151, 224, 228; 427/2.31
See application file for complete search history.

(56) References Cited

U.S. PATENT DOCUMENTS

| | | |
|---|---|---|
| 3,494,359 A | 2/1970 | Zackheim |
| 3,767,085 A | 10/1973 | Cannon et al. |
| 4,326,532 A | 4/1982 | Hammar |

(Continued)

FOREIGN PATENT DOCUMENTS

| | | |
|---|---|---|
| BE | 1008260 A6 | 2/1996 |
| EP | 0077098 A2 | 4/1983 |

(Continued)

OTHER PUBLICATIONS

European Communication dated Jun. 3, 2016 in European Patent Application No. EP 14172686.9, 5 pages.

(Continued)

*Primary Examiner* — Diane Yabut
*Assistant Examiner* — Martin T Ton

(57) ABSTRACT

The present disclosure provides filaments and/or surgical sutures which include an inner core, an outer sheath and a plurality of barbs on a surface thereof. The filaments and/or surgical sutures further include at least one adhesive precursor material which transitions from a non-adherent material to an adhesive material to attach a portion of the filament and/or suture to the surrounding area, such as tissue and/or other portions of the filament.

19 Claims, 6 Drawing Sheets

(51) Int. Cl.
  *A61B 17/12* (2006.01)
  *A61B 17/04* (2006.01)

(56) References Cited

U.S. PATENT DOCUMENTS

| | | | |
|---|---|---|---|
| 4,359,049 A | 11/1982 | Redl et al. | |
| 4,464,321 A | 8/1984 | Pittalis et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 4,898,580 A | 2/1990 | Crowley | |
| 4,915,695 A | 4/1990 | Koobs | |
| 5,021,207 A | 6/1991 | De Lucca et al. | |
| 5,104,375 A | 4/1992 | Wolf et al. | |
| 5,156,615 A | 10/1992 | Korthoff | |
| 5,254,132 A | 10/1993 | Barley | |
| 5,259,845 A | 11/1993 | Korthoff | |
| 5,259,846 A | 11/1993 | Granger | |
| 5,269,808 A | 12/1993 | Proto | |
| 5,306,288 A | 4/1994 | Granger | |
| 5,372,585 A | 12/1994 | Tiefenbrun et al. | |
| 5,425,746 A | 6/1995 | Proto | |
| 5,437,726 A | 8/1995 | Proto | |
| 5,455,308 A | 10/1995 | Bastiaansen | |
| 5,540,778 A | 7/1996 | Colligan | |
| 5,562,946 A | 10/1996 | Fofonoff et al. | |
| 5,569,302 A | 10/1996 | Proto | |
| 5,578,662 A | 11/1996 | Bennett et al. | |
| 5,582,955 A | 12/1996 | Keana et al. | |
| 5,612,050 A | 3/1997 | Rowe et al. | |
| 5,643,628 A | 7/1997 | Sonderegger | |
| 5,667,528 A | 9/1997 | Colligan | |
| 5,672,375 A | 9/1997 | Colligan | |
| 5,685,846 A | 11/1997 | Michaels, Jr. | |
| 5,728,135 A | 3/1998 | Bregen | |
| 5,753,699 A | 5/1998 | Greff | |
| 5,804,318 A | 9/1998 | Pinchuk et al. | |
| 5,891,247 A | 4/1999 | Sonderegger | |
| 5,911,942 A | 6/1999 | Fofonoff et al. | |
| 5,916,585 A | 6/1999 | Cook et al. | |
| 5,935,437 A | 8/1999 | Whitmore | |
| 5,971,953 A | 10/1999 | Bachynsky | |
| 6,099,563 A | 8/2000 | Zhong | |
| 6,107,365 A | 8/2000 | Bertozzi et al. | |
| 6,107,453 A | 8/2000 | Zuccato et al. | |
| 6,152,943 A | 11/2000 | Sawhney | |
| 6,165,201 A | 12/2000 | Sawhney | |
| 6,179,862 B1 | 1/2001 | Sawhney | |
| 6,214,332 B1 | 4/2001 | Askill | |
| 6,224,571 B1 | 5/2001 | Bierman | |
| 6,264,675 B1 | 7/2001 | Brotz | |
| 6,312,725 B1 | 11/2001 | Wallace et al. | |
| 6,325,804 B1 | 12/2001 | Wenstrom | |
| 6,342,213 B1 | 1/2002 | Barley | |
| 6,342,591 B1 | 1/2002 | Zamora et al. | |
| 6,406,455 B1 | 6/2002 | Willis et al. | |
| 6,451,032 B1 | 9/2002 | Ory et al. | |
| 6,514,534 B1 | 2/2003 | Sawhney | |
| 6,534,611 B1 | 3/2003 | Darling et al. | |
| 6,552,103 B1 | 4/2003 | Bertozzi et al. | |
| 6,566,406 B1 | 5/2003 | Pathak et al. | |
| 6,570,040 B2 | 5/2003 | Saxon et al. | |
| 6,576,000 B2 | 6/2003 | Carrison | |
| 6,605,294 B2 | 8/2003 | Sawhney | |
| 6,624,245 B2 | 9/2003 | Wallace et al. | |
| 6,667,031 B2 | 12/2003 | Azevedo | |
| 6,673,093 B1 | 1/2004 | Sawhney | |
| 6,699,940 B2 * | 3/2004 | Shalaby | A61L 24/06 525/255 |
| 6,703,047 B2 | 3/2004 | Sawhney | |
| 6,805,876 B2 | 10/2004 | Leong et al. | |
| 6,818,018 B1 | 11/2004 | Sawhney | |
| 6,849,082 B2 | 2/2005 | Azevedo | |
| 6,881,766 B2 | 4/2005 | Hain | |
| 6,958,212 B1 | 10/2005 | Hubbell et al. | |
| 7,009,034 B2 | 3/2006 | Pathak et al. | |
| 7,012,126 B2 | 3/2006 | Matsuda et al. | |
| 7,105,629 B2 | 9/2006 | Matsuda et al. | |
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,347,850 B2 | 3/2008 | Sawhney | |
| 7,371,719 B2 | 5/2008 | Stupp et al. | |
| 7,375,234 B2 | 5/2008 | Sharpless et al. | |
| 7,560,588 B2 | 7/2009 | Breitenkamp et al. | |
| 7,618,944 B2 | 11/2009 | Breitenkamp et al. | |
| 7,638,558 B2 | 12/2009 | Breitenkamp et al. | |
| 7,650,588 B2 | 1/2010 | Ivansen | |
| 7,667,012 B2 | 2/2010 | Saxon et al. | |
| 7,740,646 B2 | 6/2010 | Hunt | |
| 7,795,355 B2 | 9/2010 | Matyjaszewski et al. | |
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 8,034,396 B2 | 10/2011 | Kapiamba et al. | |
| 8,062,330 B2 | 11/2011 | Prommersberger et al. | |
| 8,118,834 B1 * | 2/2012 | Goraltchouk | A61B 17/06166 606/228 |
| 8,124,165 B2 | 2/2012 | Tsai | |
| 8,142,475 B2 | 3/2012 | Viola | |
| 8,496,683 B2 | 7/2013 | Prommersberger | |
| 2002/0016003 A1 | 2/2002 | Saxon et al. | |
| 2002/0049503 A1 | 4/2002 | Milbocker | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2002/0173770 A1 | 11/2002 | Flory | |
| 2003/0050590 A1 | 3/2003 | Kirsch | |
| 2003/0100086 A1 | 5/2003 | Yao et al. | |
| 2003/0135238 A1 | 7/2003 | Milbocker | |
| 2003/0153948 A1 | 8/2003 | Morrison | |
| 2003/0162903 A1 | 8/2003 | Day | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2004/0249438 A1 | 12/2004 | Lefranc et al. | |
| 2005/0032081 A1 | 2/2005 | Ju et al. | |
| 2005/0038472 A1 | 2/2005 | Furst | |
| 2005/0113869 A1 | 5/2005 | Price | |
| 2005/0142172 A1 | 6/2005 | Kirsch et al. | |
| 2005/0148032 A1 | 7/2005 | Saxon et al. | |
| 2005/0222427 A1 | 10/2005 | Sharpless et al. | |
| 2005/0233389 A1 | 10/2005 | Ting et al. | |
| 2005/0244453 A1 | 11/2005 | Stucke et al. | |
| 2006/0018948 A1 | 1/2006 | Guire et al. | |
| 2006/0036022 A1 | 2/2006 | Callaghan et al. | |
| 2006/0050262 A1 | 3/2006 | Poon et al. | |
| 2006/0085033 A1 | 4/2006 | Criscuolo et al. | |
| 2006/0085036 A1 | 4/2006 | Viola | |
| 2006/0108393 A1 | 5/2006 | Heinrich et al. | |
| 2006/0110782 A1 | 5/2006 | Bertozzi et al. | |
| 2006/0142404 A1 | 6/2006 | Berge et al. | |
| 2006/0147963 A1 | 7/2006 | Barone et al. | |
| 2006/0189944 A1 | 8/2006 | Campbell et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0005020 A1 | 1/2007 | Laveault | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0140966 A1 | 6/2007 | Chang et al. | |

(56) References Cited

U.S. PATENT DOCUMENTS

| | | |
|---|---|---|
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0233188 A1 | 10/2007 | Hunt |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0058869 A1 | 3/2008 | Stopek |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0024097 A1 | 1/2009 | Okoniewski |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0112236 A1 | 4/2009 | Stopek |
| 2009/0124534 A1 | 5/2009 | Reineke et al. |
| 2009/0137424 A1 | 5/2009 | Tsao et al. |
| 2009/0143816 A1* | 6/2009 | Boyden ............ A61B 17/00491 606/214 |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0259233 A1* | 10/2009 | Bogart ............ A61B 17/06004 606/144 |
| 2009/0263468 A1 | 10/2009 | McaNulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0080838 A1 | 4/2010 | Stopek |
| 2010/0098640 A1 | 4/2010 | Cohen et al. |
| 2010/0104589 A1 | 4/2010 | Govindan et al. |
| 2010/0104608 A1 | 4/2010 | Abuzaina |
| 2010/0121022 A1 | 5/2010 | Musa et al. |
| 2010/0155454 A1 | 6/2010 | Viola |
| 2010/0159508 A1 | 6/2010 | Yang et al. |
| 2010/0185219 A1 | 7/2010 | Gertzman |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0087272 A1* | 4/2011 | Sargeant ............ A61B 17/0057 606/213 |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |
| 2012/0031950 A1 | 2/2012 | Prommersberger |
| 2012/0150221 A1 | 6/2012 | Viola |
| 2012/0277773 A1 | 11/2012 | Sargeant |
| 2013/0226236 A1 | 8/2013 | Kim |
| 2013/0310873 A1 | 11/2013 | Stopek et al. |
| 2014/0213966 A1 | 7/2014 | Ostapoff |

FOREIGN PATENT DOCUMENTS

| | | |
|---|---|---|
| EP | 0328050 A2 | 8/1989 |
| EP | 0490854 B1 | 9/1996 |
| EP | 1790702 A1 | 5/2007 |
| EP | 1795563 A1 | 6/2007 |
| EP | 2014308 A2 | 1/2009 |
| EP | 2090592 A1 | 8/2009 |
| EP | 2380599 A2 | 10/2011 |
| EP | 2567714 A1 | 3/2013 |
| EP | 2759266 A2 | 7/2014 |
| WO | WO 99/11692 A1 | 3/1999 |
| WO | WO 99/28354 A1 | 6/1999 |
| WO | WO 00/62827 A2 | 10/2000 |
| WO | WO 01/68565 A2 | 9/2001 |
| WO | WO 03/101972 A1 | 12/2003 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/002109 A2 | 1/2007 |
| WO | WO 2007/003054 A1 | 1/2007 |
| WO | WO 2007/011696 A2 | 1/2007 |
| WO | WO 2007/011967 A2 | 1/2007 |
| WO | WO 2007/021762 A2 | 2/2007 |
| WO | WO 2007/021763 A2 | 2/2007 |
| WO | WO 2007/022070 A2 | 2/2007 |

(56) References Cited

FOREIGN PATENT DOCUMENTS

| WO | WO 2007/027493 A2 | 3/2007 |
|---|---|---|
| WO | WO 2007/035296 A2 | 3/2007 |
| WO | WO 2007/039858 A2 | 4/2007 |
| WO | WO 2007/041394 A2 | 4/2007 |
| WO | WO 2007/041451 A2 | 4/2007 |
| WO | WO 2007/046893 A2 | 4/2007 |
| WO | WO 2007/047301 A2 | 4/2007 |
| WO | WO 2007/047609 A2 | 4/2007 |
| WO | WO 2007/047668 A2 | 4/2007 |
| WO | WO 2007/047796 A2 | 4/2007 |
| WO | WO 2007/056561 A2 | 5/2007 |
| WO | WO 2007/075270 A2 | 7/2007 |
| WO | WO 2007/081876 A2 | 7/2007 |
| WO | WO 2007/104948 A2 | 9/2007 |
| WO | WO 2007/112193 A2 | 10/2007 |
| WO | WO 2007/121055 A1 | 10/2007 |
| WO | WO 2007/125429 A2 | 11/2007 |
| WO | WO 2007/127473 A2 | 11/2007 |
| WO | WO 2007/132000 A1 | 11/2007 |
| WO | WO 2007/132005 A2 | 11/2007 |
| WO | WO 2008/004988 A1 | 1/2008 |
| WO | WO 2008/006097 A2 | 1/2008 |
| WO | WO 2008/008483 A2 | 1/2008 |
| WO | WO 2008/011335 A2 | 1/2008 |
| WO | WO 2008/013618 A1 | 1/2008 |
| WO | WO 2008/016371 A2 | 2/2008 |
| WO | WO 2008/017029 A2 | 2/2008 |
| WO | WO 2008/019450 A1 | 2/2008 |
| WO | WO 2008/024435 A2 | 2/2008 |
| WO | WO 2008/031525 A1 | 3/2008 |
| WO | WO 2008/036350 A2 | 3/2008 |
| WO | WO 2008/047057 A1 | 4/2008 |
| WO | WO 2008/048288 A2 | 4/2008 |
| WO | WO 2008/048733 A1 | 4/2008 |
| WO | WO 2008/060333 A1 | 5/2008 |
| WO | WO 2008/075955 A2 | 6/2008 |
| WO | WO 2008/077406 A2 | 7/2008 |
| WO | WO 2008/088658 A2 | 7/2008 |
| WO | WO 2008/091349 A1 | 7/2008 |
| WO | WO 2008/094254 A2 | 8/2008 |
| WO | WO 2008/101024 A2 | 8/2008 |
| WO | WO 2008/101069 A1 | 8/2008 |
| WO | WO 2008/105773 A2 | 9/2008 |
| WO | WO 2008/105902 A2 | 9/2008 |
| WO | WO 2008/106657 A2 | 9/2008 |
| WO | WO 2008/108736 A1 | 9/2008 |
| WO | WO 2008/115694 A2 | 9/2008 |
| WO | WO 2008/120016 A1 | 10/2008 |
| WO | WO 2008/121375 A2 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |
| WO | WO 2010/095049 A1 | 8/2010 |

OTHER PUBLICATIONS

European Search Report, Application No. EP 14 17 2686 dated Nov. 10, 2014.
Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008) ; (Abstract Only).
R. Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.
Sletten and Bertozzi, "A Hydrophilic Azacyclooctyne for Cu-free Click Chemistry", Org. Lett. (2008) 10(14), pp. 3097-3099.
Cazalis, et al., "C-Terminal Site-Specific PEGylation of a Truncated Thrombomodulin Mutant with Retention of Full Bioactivity", Bioconjugate Chem., (2004), 15, pp. 1005-1009.
Haridas, et al., "Design and Synthesis of Triazole-based Peptidedendrimers" Tetrahedron Letters, vol. 48, (2007), pp. 4719-4722.
Raghavan, et al., "Chemical Probes for Profiling Fatty Acid-associated Proteins in Living Cells", Bioorg. Med. Chem. Lett., 18 (2008), pp. 5982-5986.
Le Dévédec, et al., "Separation of Chitosan Oligomers by Immobilized Metal Affinity Chromatography", Journal of Chromatography A., 2008, 1194(2), pp. 165-171.
Hartgerink, et al., "Peptide-amphiphile Nanofibers: A Versatile Scaffold For the Preparation of Self Assembling Materials", PNAS, 2002; 99(2), pp. 5133-5138.
Van Berkel, et al., "Metal-Free Triazole Formation as a Tool for Bioconjugation" Chem Bio Chem, 8, (2007), pp. 1504-1508.
Nottelet, et al., Synthesis of an X-ray opaque biodegradable copolyester by chemical modification of poly (ε-caprolactone) Biomaterials, 27, (2006), pp. 4943-4954.
Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863; (Abstract Only).
Skierka, et al., "The Influence of Different Acids and Pepsin on the Extractability of Collagen From the Skin of Baltic Cod (*Gadus Morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.
Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461; (Abstract Only).
Srinivasachari, et al., "Versatile Supramolecular pDNA Vehicles via "Click Polymerization" of β-cyclodextrin with oligoethyleneamines", Biomaterials, 30, (2009), pp. 928-938.
Arora, et al., "A Novel domino-click approach for the synthesis of sugar based unsymmetrical bis-1,2,3-triazoles", Carbohydrate Research, 343, (2008), 139-144.
Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045; (Abstract Only).
Srinivasachari, et al., "Effects of Trehalose Click Polymer Length on pDNA Complex Stability and Delivery Efficacy", Biomaterials, 28, (2007), pp. 2885-2898.
Godeau, et al., Lipid-Conjugated Oligonucleotides via "Click Chemistry" Efficiently Inhibit Hepatitis C Virus Translation, J. med. Chem., 2008, 51(15), pp. 2374-4376; (Abstract Only).

(56) References Cited

OTHER PUBLICATIONS

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via $i$ to $i + 4$ Intramolecular Side-chain to Side-chain Azide-Alkyne 1,3-Dipolar Cycloaddition" J. Org. Chem., 2008, 73 (15), pp. 5663-5614; (Abstract Only).

Dijk, et al., "Synthesis of Peptide-Based Polymers by Microwave-Assisted Cycloaddition Backbone Polymerization, "Biomacro molecules, 2007, 8(2), pp. 327-330; (Abstract Only).

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332; (Abstract Only).

Dijk, et al., "Synthesis and Characterization of Biodegradable Peptide-Baed Polymers Prepared by Microwave-Assisted Click Chemisty", Biomacromolecules, 2008, 9(10), pp. 2834-2843; (Abstract Only).

Jiang, et al., "Amphiphilic PEG/alkyl-grafted comb polylactides", J. Polymer Science Part B: Polymer Physics, 45(22), 2007, pp. 5227-5236; (Abstract Only).

Ochs, Et Al., "Low-Fouling, Biofunctionalized, and Biodegradable Click Capsules", Biomacromolecules, 2008, 9(12), pp. 3389-3396; (Abstract Only).

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081; (Abstract Only).

Nandivada, et al. "Reactive polymer coatings that 'Click'", Angewandte Chemie, International Edition 45, Apr. 2006, pp. 3360-3363; (Abstract Only).

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

* cited by examiner

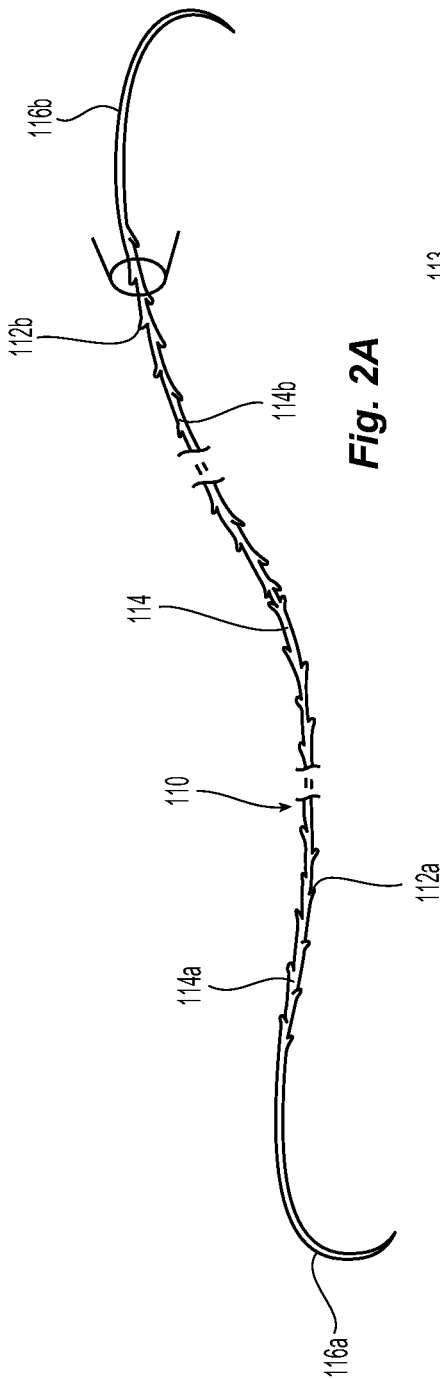
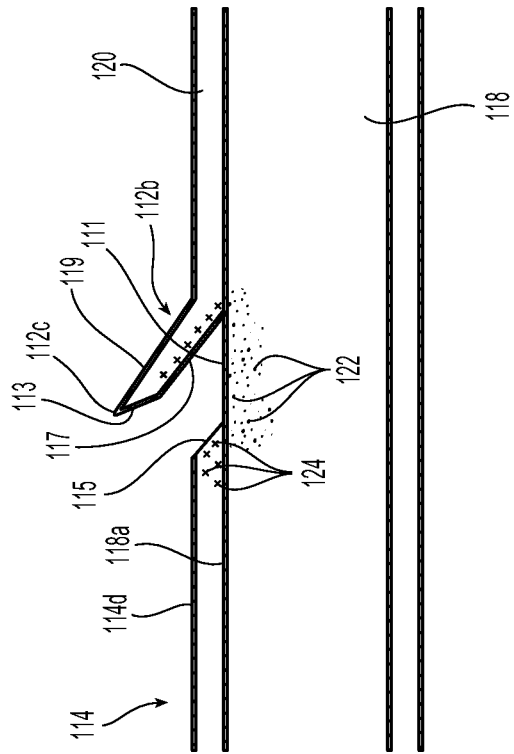
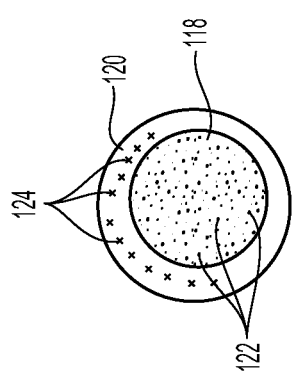
Fig. 2A
Fig. 2B
Fig. 2C

ADHESIVE BARBED FILAMENT

CROSS-REFERENCE TO RELATED APPLICATIONS

This application claims the benefit of and priority to U.S. Provisional Patent Application No. 61/836,374, filed Jun. 18, 2013, the entire disclosure of which is incorporated by reference herein.

BACKGROUND

Technical Field

The present disclosure provides filaments and particularly barbed filaments which can adhere directly to tissue following implantation.

Background of Related Art

Filaments may be used to form sutures which are frequently used to close or bind wounds in human or animal tissue. Conventional sutures can be a smooth monofilament or can be a multi-filament, and can be formed from non-absorbable material such as silk, nylon, polyester, polypropylene, or cotton, or can be formed from bio-absorbable material such as glycolic acid polymers and copolymers or lactic acid polymers and copolymers.

Barbed sutures are generally formed from the same materials as conventional sutures, and offer several advantages for closing wounds compared with conventional sutures. Barbed sutures include barbs that project from the surface of the filament body along the body length. The barbs are arranged to allow passage of the barbed suture in one direction through tissue but resist movement in the opposite direction.

Various methods of forming barbs on filaments or sutures are known in the art. For example, barbs may be produced by cutting into the filament or suture material. By cutting into the body of the filament, the diameter of the filament may be significantly narrowed near the area of the barb, which can weaken the mechanical strength of the filament. Any stress applied by the tissue to the barbed filament following implantation can potentially lead to either: breaking of the body of the filament along the narrowed diameter portion of the filament, and/or, failing of the barb which extends away from the body of the filament because the narrowed body of the filament near the barb can not properly support the barb under a certain level of stress. For example, following implantation the tissue, due to body movement, can apply stress to the filament body and the barbs which can lead to tearing and/or destabilization of the filament and/or the wound. Breakages in the filament can occur in extreme cases.

It could therefore be helpful to provide a barbed filament which not only resists movement in a direction opposite the barbs, but also enhances the mechanical strength of the suture by adhering directly to the surrounding tissue following implantation, and specifically near the location of the barb and/or the narrowed diameter of the filament to provide additional support and prevent premature tearing, destabilization and/or breakage of the filament.

SUMMARY

The present disclosure provides a barbed filament and/or suture which can adhere directly to the surrounding tissue following implantation, and specifically, near the barbed portions of the implant. It is envisioned that the adhering the body of the barbed filament to the surrounding tissue may distribute stress more evenly along the length of the filament and away from the barb which may improve suture retainment, and reduce barb failure and/or wound destabilization.

The surgical sutures described herein include at least one filament having an elongated body including an inner core and outer sheath, the inner core including an adhesive precursor. A plurality of barbs are formed along a surface of the elongated body and expose a portion of the inner core and the adhesive precursor to the surrounding tissue.

The adhesive precursor includes any suitable material which can transition from a non-adherent material to an adherent material, such as an adhesive, sealant and/or hydrogel.

In embodiments, the filament includes a single adhesive precursor, which following implantation, may interact with the normal bodily fluids found at the site of implantation and adhere the filament to the tissue. In embodiments, the filament may include two or more adhesive precursors which upon implantation may mix and/or interact with each other to form an adherent material which attaches the filament to the tissue. In embodiments, the adhesive precursor may alternatively be used to attach one portion of the filament to another over-lapping portion of the filament, such as when a suture knot is formed.

A method of forming a surgical suture is also disclosed. The method includes providing a filament having an elongate body and including an inner core and an outer sheath, the inner core including at least one adhesive precursor, and, forming a plurality of barbs on a surface of the filament which expose a portion of the inner core including the adhesive precursor to allow the inner core to adhere to tissue following implantation.

DESCRIPTION OF THE DRAWINGS

Various embodiments of the presently disclosed barbed filaments are disclosed herein with reference to the drawings, wherein:

FIG. 2A is a perspective view of a surgical suture including a barbed filament as described in at least one embodiment herein;

FIGS. 2B and 2C are a cross-sectional view of the surgical suture described in FIG. 2A;

DETAILED DESCRIPTION

The present disclosure describes surgical sutures including at least one filament having an inner core including at least one adhesive precursor and an outer sheath positioned around the inner core. At least one barb is positioned along a surface of the filament and configured to penetrate the outer sheath and expose a portion of the inner core including the adhesive precursor.

Exposure of the inner core and the adhesive precursor in the vicinity of the barb allows the filament to adhere to the surrounding tissue following implantation via the activation and/or transition of the adhesive precursor from a non-adherent material to an adherent material.

Adherence of the filament to the tissue at or near the inner core and/or near the site of the barb(s) may strengthen the filament and/or prevent breakage of the filament and/or barbs due to the reduced stress applied by the tissue to the reduced diameter portion of the filament and/or the barb portion.

Figure 1A:
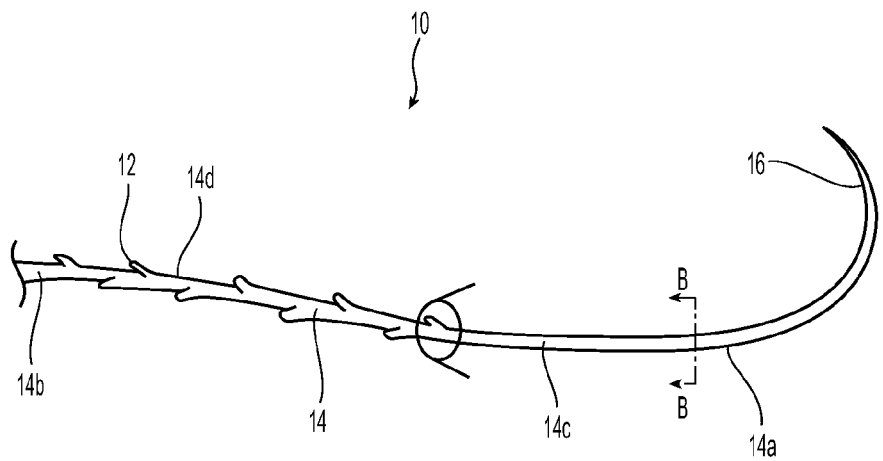
FIG. 1A is a perspective view of a surgical suture including a barbed filament as described in at least one embodiment herein.
Figure 1B:
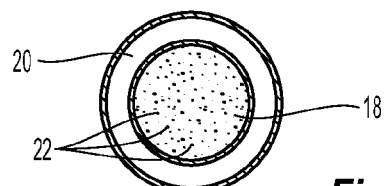
FIGS. 1B and 1C are a cross-sectional view of the surgical suture described in FIG. 1A.
Figure 1C:
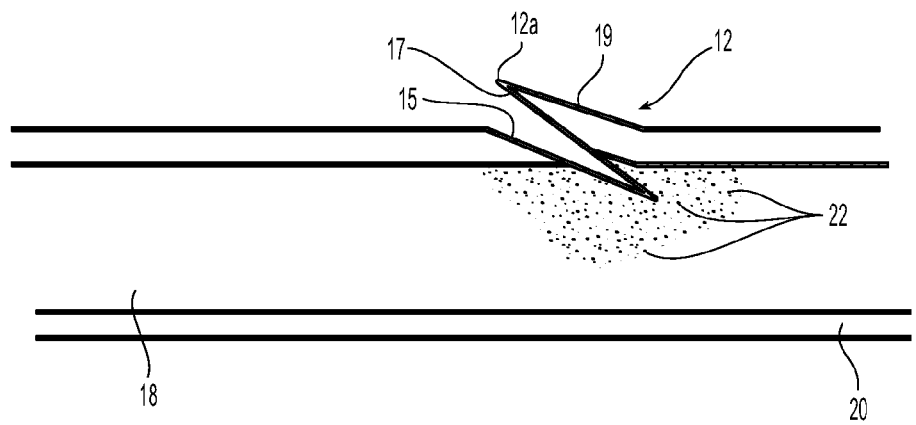

Turning now to FIGS. 1A-1C, surgical suture 10, made from any suitable biocompatible polymeric material, is schematically shown as a single filament 14 having elongate body 14c positioned between proximal end 14a and distal end 14b. Surgical needle 16 is shown attached to proximal end 14a of filament 14 rendering suture 10 a single-armed suture.

Filament 14 further includes inner core 18 which includes at least one adhesive precursor 22 and outer sheath 20 which is positioned around inner core 18. A plurality of barbs 12 are positioned along a surface 14d of filament 14. In embodiments, all of the barbs 12 may be aligned to allow the suture to move through tissue in one direction and resist moving through tissue in the opposite direction. For example, referring to FIG. 1A, the plurality of barbs 12 on suture 10 may be formed into a uni-directional suture. In embodiments, the plurality of barbs 12 permit movement of suture 10 through tissue in a distal-to-proximal direction, i.e., with the needle or proximal end of the suture leading the way through tissue. In embodiments, the plurality of barbs 12 are generally rigid in an opposite direction and prevent movement of suture 10 in a proximal-to-distal direction, i.e., with the distal end of the suture leading the way through the tissue.

As depicted in FIG. 1C, the plurality of barbs 12 penetrate through outer sheath 20 and expose at least a portion of inner core 18 including the adhesive precursor(s) 22. Barb formation may create body inner surface 15, barb inner surface 17 and barb outer surface 19. Body inner surface 15 extends inwardly from outer surface 14d of filament 14 to a depth sufficient to expose a portion of inner core 18. Barb inner surface 17 extends outwardly from inner core 18 from body inner surface 15 at an angle less than 90 degrees and beyond outer surface 14d of filament 14. Outer barb surface 19 connects the outermost tip 12a of barb 12 to outer surface 14d of filament 14.

As further depicted in FIG. 1C, body inner surface 15 and barb inner surface 17 each include a portion of outer sheath 18 and a portion of inner core 20. In embodiments, exposure of the adhesive precursor via the depth and/or configuration of the barb allows access for aqueous fluids, such as endogenous fluids, to interact with the inner core and the adhesive precursor.

In embodiments, the aqueous fluids may assist with the transition of the precursor from a non-adherent material to an adherent material. By changing the angle and/or the depth of which body inner surface 15 extends into filament 14 and/or barb inner surface extends outwardly away from inner core 18 of filament 14, one can control the amount of adhesive precursor which is exposed to the surrounding tissue. It is envisioned that increasing the surface area of inner core 18 exposed to the surrounding tissue at the site of implantation increases the adherent strength of the suture to the tissue.

In FIGS. 2A-2C, surgical suture 110, made from any suitable biocompatible material, is schematically shown as a single filament 114 having elongate body 114c positioned between a first portion 114a and a second portion 114b of filament 114. First and second surgical needles 116a and 116b are shown attached to first and second portions 114a and 114b, respectively, rendering suture 110 a double-armed or multi-armed suture.

Filament 114 further includes inner core 118 which includes a first adhesive precursor 122 and outer sheath 120 which is positioned around inner core 118 and includes a second adhesive precursor 124. In embodiments, the first and second adhesive precursors 122 and 124 may represent individual reactive materials of a two-part adhesive or sealant. For example, and as described in more detail hereinbelow, the first adhesive precursor may include a first material including pendant electrophilic groups and the second adhesive precursor may include a second material including pendant nucleophilic groups capable of reacting with the electrophilic groups of the first material to form an adherent or sealant when combined.

In embodiments, the first and second adhesive precursors 122 and 124 may be released from their respective core and sheath layers upon exposure to aqueous fluids and/or degradation of their respective layers. In embodiments, the first and second precursors may need to interact with each other to become an adherent material.

A plurality of barbs 112a and 112b are positioned along filament 114. In embodiments, a first set of barbs 112a may be aligned on first portion 114a to allow movement of suture 110 through tissue in one direction, while a second set of barbs 112b may be aligned on second portion 114b to allow movement of suture 110 through tissue in a second opposite direction. For example, as depicted in FIG. 2A, suture 110 may be a bi-directionally barbed suture.

As depicted in FIG. 2C, barbs 112b may include compound barbs which penetrate through outer sheath 120 and expose at least a portion of inner core 118 including the adhesive precursor(s) 122. Compound barb formation creates barbs having multiple surfaces and/or angles. For example, as further shown in FIG. 2C, barbs 112b include first and second body inner surfaces 115 and 111, first and second barb inner surface 117 and 113 and barb outer surface 119. In embodiments, first body inner surface 115 extends inwardly from outer surface 114d of filament 114 to a depth sufficient to expose a portion of inner core 118 without penetrating inner core 118. In embodiments, second body inner surface 111 extends along outer edge 118a of inner core 118 exposing outer edge 118a of inner core 118 for a predetermined length.

First barb inner surface 117 extends outwardly from outer edge 118a of inner core 118 and/or second body inner surface 111 at an angle less than 90 degrees. Second barb inner surface 113 extends beyond outer surface 114d from first barb inner surface 117. Outer barb surface 119 connects the outermost tip 112c of barbs 112b to outer surface 114d of filament 114.

As further depicted in FIG. 2C, first body inner surface 115, first barb inner surface 117 and second barb inner surface 113 each consist of only outer sheath 120 which includes second adhesive precursor 124. Second inner body surface 111 consists of only inner core 118 and first adhesive precursor 122. Spatial separation by layer of the first and second adhesive precursors is only one of a variety of ways of preventing the premature interaction of the precursors prior to implantation and/or use.

Figure 3:
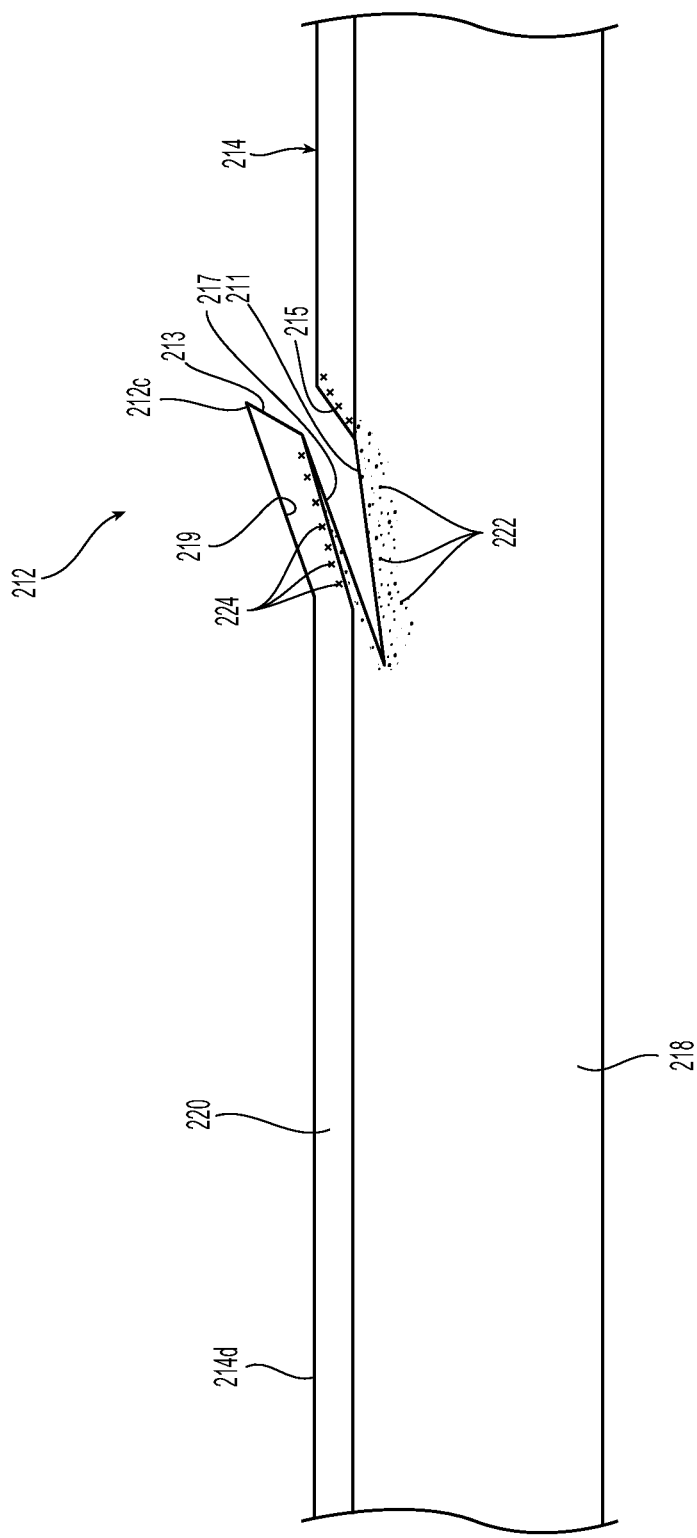
FIG. 3 is a cross-sectional view of a surgical suture described in yet another embodiment.

In FIG. 3, surgical suture 210 is schematically shown including at least one filament 214 including inner core 218, outer core 220 and at least one barb 212. First adhesive precursor 222 is located within inner core 218 and second adhesive precursor 224 is located within outer core 220.

Barb 212 includes a compound barb which penetrates through outer sheath 220 from outer surface 214d and exposes at least a portion of inner core 218 including the adhesive precursor(s) 222. Barb 212 includes first and second body inner surfaces 215 and 211, first and second barb inner surface 217 and 213 and barb outer surface 219. Outer barb surface 219 connects the outermost tip 212c of barb 212 to outer surface 214d of filament 214.

In embodiments, first body inner surface 215 extends inwardly from outer surface 214d of filament 214 to a depth sufficient to expose a portion of inner core 218, with or without initially penetrating inner core 218. In embodiments, second body inner surface 211 extends deeper into inner core 218 creating a compound barb with second body inner surface 211 and first inner barb surface 217 consisting entirely of and/or predominantly of inner core 218 and first adhesive precursor 222. In embodiments, first inner body surface 215 and second barb inner surface 213 consist entirely and/or predominantly of outer sheath 220 which may include second adhesive precursor 222. It is envisioned that the increased surface area of exposure to the inner core 218 and the adhesive precursor, along first inner barb surface 217 and second inner body surface 211, will increase the amount of active adhesive centrally near the core of the filament, rather than near the barb 212 and distal tip 212c.

Figure 4:
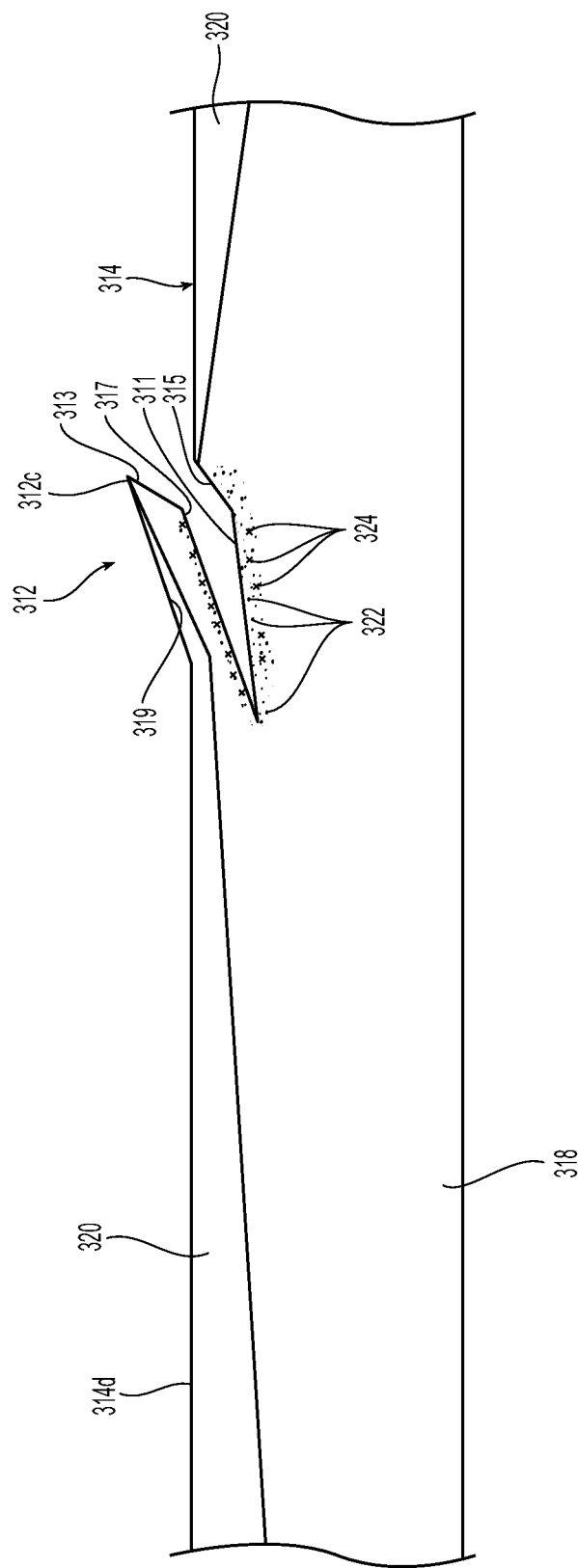
FIG. 4 is a cross-sectional view of a surgical suture described in yet another embodiment.
Figure 5A:
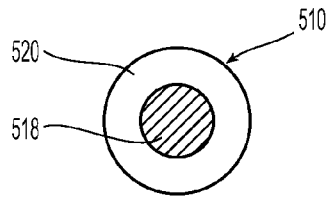
FIGS. 5A-5E are a cross-sectional view of a variety of filaments described herein; and, FIG. 6 is a perspective view of a surgical mesh including a barbed filament as described herein.
Figure 5D:
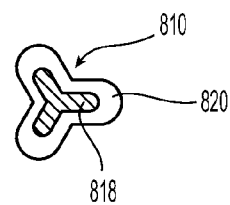
Figure 5B:
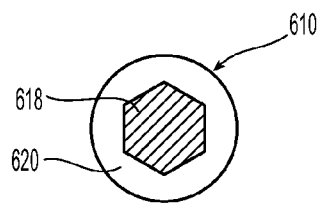
Figure 5E:
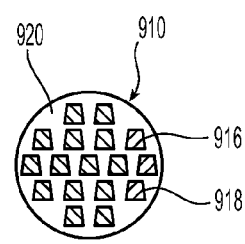
Figure 5C:
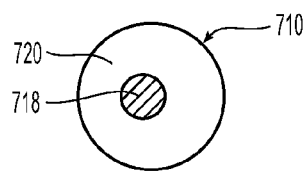

In FIG. 4, surgical suture 310 is schematically shown including at least one filament 314 including inner core 318, outer sheath 320 and at least one barb 312. First adhesive precursor 322 and second adhesive precursor 324 are located within inner core 318. Outer sheath 320 surrounds inner core 318 in a discontinuous and/or uneven manner.

As depicted in FIG. 4, barb 312 penetrates through inner core 318 only. In embodiments, barb 312 may penetrate a very thin layer of outer sheath 320. Barb 312 includes first and second body inner surfaces 315 and 311, and first and second barb inner surface 317 and 313 all which include entirely and/or predominantly of inner core 318 and first and second adhesive precursors 322 and 324. Outer barb surface 319 includes outer core 320 and connects the outermost tip 312c of barb 312 to outer surface 314d of filament 314.

It is envisioned that the increased surface area of exposure to the inner core 318 and the adhesive precursors, along second inner barb surface 317 may increase the amount of active adhesive near the distal tip 312c of barb 312.

As shown in FIGS. 1-4, each suture comprises, consists of and/or consists essentially of at least one barbed filament of a core/sheath construction. It should be recognized that although the core/sheath filaments depicted in each of FIGS. 1-4 are generally circular in cross-section, any variety of regular and irregular cross sectional shapes may be encompassed by the present disclosure, such as, by way of example and not by limitation, multi-lobal, octagonal, oval, pentagonal, rectangular, square-shaped, trapezoidal, triangular, wedge-shaped, and so forth. Various non-limiting examples are further shown in FIGS. 5A-5G.

Filament 510 includes inner core 518 positioned within and surrounded by outer sheath 520. Here, inner core 518 is generally centered within outer sheath 520. Filament 510 includes about 25 percent by weight of the core and about 75 percent by weight of the sheath.

Filament 610 includes inner core 618 positioned within and surrounded by outer sheath 620. Here, inner core 618 is a different cross sectional shape than outer sheath 620. More specifically, the cross-sectional shape of inner core 618 is hexagonal and outer sheath 620 is generally circular. Any combination of different shapes and designs are also considered suitable for the filaments described herein.

Filament 710 includes inner core 718 positioned within and surrounded by outer sheath 720. Here, inner core 718 is eccentrically and/or not generally centered within outer sheath 720. Filament 710 includes about 5-20 percent by weight of the core and about 80-95 percent by weight of the sheath.

Tri-lobal filament 810 includes a tri-lobal inner core 818 positioned within and surrounded by tri-lobal outer sheath 820. Filament 810 includes about 50 percent by weight of the core and about 50 percent by weight of the sheath.

It should be recognized that the inner core and/or the outer sheath may, in general, have a variety of regular or irregular cross sectional shapes, such as, by way of example and not by limitation, circular, multi-lobal, octagonal, oval, pentagonal, rectangular, square-shaped, trapezoidal, triangular, wedge-shaped, and so forth. While filaments 510, 610, 710 and 810 are shown with one inner core member positioned within and surrounded by a sheath member, it should be recognized that two or more core members may be positioned within and surrounded by a sheath member (e.g., in a manner similar to that shown for filament 910).

Filament 910 includes a plurality of inner core members 916, 918 positioned within and surrounded by outer sheath 920. A first set of inner core members 916 may include a first adhesive precursor and a second set of inner core members 918 may include a second adhesive precursor. In such embodiments, the plurality of adhesive precursors are separated by outer sheath 920 being positioned between the first and second set of inner core members 916, 918 to prevent premature interaction between the multiple adhesive precursors.

The filaments and/or sutures described herein may be formed using any technique within the purview of those skilled in the art, such as, for example, extrusion, molding, spinning and/or solvent casting. In some embodiments, the suture may include a single filament. In some embodiments, the suture may include multiple filaments. In some embodiments, the suture may include a yarn made of multiple filaments, which include at least one of the filaments described herein, and which may further contain one or more filaments of different design and/or material(s). For example, in embodiments, the barbed filaments described herein may be combined with filaments made from ultra-high molecular weight polyethylene to form a high-strength self-adhering yarn. Where the suture is made of multiple filaments, the suture may be made using any known technique such as, for example, braiding, weaving or knitting, drawing, entangling, twisting, commingling, and the like. In one embodiment, a multifilament suture may be produced by braiding. The braiding may be done by any method within the purview of those skilled in the art.

The sutures and other fibrous implantable medical devices described herein may be monofilament or multifilament. Furthermore, the suture and other fibrous implantable medical devices may include portions which are monofilament and portions which are multifilament.

In embodiments, the inner core and the outer sheath of the filament may be formed together via any suitable process, such as co-extrusion. In embodiments, the inner core and outer sheath may be formed individually and may be combined after formation. In still other embodiments, the outer sheath may be a coating or layer which is applied to the inner core using any suitable method of coating, including, dipping, spraying, brushing, wiping, and the like.

The inner core and outer sheath of the filaments described herein may be made from any fiber-forming biocompatible polymeric material. The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Representative natural biodegradable polymers which may be used include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers which may be used include: cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers suitable for use include: polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like); dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the filaments may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Rapidly biodegradable polymers, such as poly(lactide-co-glycolide)s, polyanhydrides, and polyorthoesters, which have carboxylic groups exposed on the external surface as the smooth surface of the polymer erodes, may also be used. It should, of course, be understood that any combination of natural, synthetic, biodegradable, and non-biodegradable materials may be used to form any of the inner core and/or outer sheath of the filaments of the present disclosure.

The filaments of the present disclosure also include at least one barb, and in embodiments, a plurality of barbs. The barbs can be arranged in any suitable pattern, for example, in a helical pattern. The number, configuration, spacing and surface area of the barbs can vary depending upon the tissue in which the filament is used, as well as the composition and geometry of the material utilized to form the filament. Additionally, the proportions of the barbs may remain relatively constant while the overall length of the barbs and the spacing of the barbs may be determined by the tissue being connected. For example, if the filament is to be used to connect the edges of a wound in skin or tendon, the barbs may be made relatively short and more rigid to facilitate entry into this rather firm tissue. Alternatively, if the filament is intended for use in fatty tissue, which is relatively soft, the barbs may be made longer and spaced further apart to increase the ability of the filament to grip the soft tissue.

The barbs may be formed on the filaments using any technique within the purview of those skilled in the art, such as, for example, hand-cutting, laser-cutting, ultrasonics or mechanically machine-cutting using blades, cutting wheels, grinding wheels, molding, and so forth. In some embodiments, barbs may be formed by making acute angular cuts directly into the elongate body of the filament and through the outer sheath, with cut portions pushed outwardly and separated from the inner core of the filament. The depth of the barbs thus formed may depend on the dimensions of the outer sheath and inner core of the filament. In some embodiments, compound barbs may be formed in the filament, which include more than one cut into the elongate body of the filament.

In embodiments, the filament may be in a fixed position while the barbs are cut into the filament. In embodiments, the filament may be moving while the barbs are cut into the filament.

The filaments described herein further include at least one adhesive precursor. As used herein the term "adhesive precursor" may be used to refer to materials which are initially non-adherent and which transition to an adherent state following implantation. In embodiments, an adhesive precursor may be a monomer, an oligomer, or a macromer. As used herein the terms "adhesive precursor(s)", "first adhesive precursor", and "second adhesive precursor" may be used to refer to components that alone or in combination may form an adhesive, sealant and/or a hydrogel, to adhere the filament to the surrounding tissue and/or other portions of the filament, such as when tying a knot. For example, in some embodiments, the adhesive precursor may a material which when combined with the endogenous fluids located at the site of implantation, such as blood, sweat, mucus, tears, water, saline, transitions from a non-adherent material to an adherent material. In some embodiments, the adhesive precursor may include a cyanoacrylate which following implantation will react with the endogenous fluids and polymerize and adhere to tissue.

In embodiments, the addition of a catalyst or an initiator may be utilized to transition the non-adherent material(s) to an adherent state.

In embodiments, adhesive precursors may include combinations of reactive adhesive precursors and initiated adhesive precursors. As used herein the terms "reactive adhesive precursor(s)", "first reactive adhesive precursor(s)", and "second reactive adhesive precursor(s)" include precursors that may crosslink upon exposure to each other to form an adhesive, sealant and/or hydrogel. As used herein the term "initiated adhesive precursor(s)", "first initiated adhesive precursor(s)" and "second initiated adhesive precursor(s)" may be used to describe first and second precursors that crosslink upon exposure to an external source, sometimes referred to herein as an "initiator". Initiators include, for example, ions, UV light, redox-reaction components, combinations thereof, as well as other initiators within the purview of those skilled in the art.

The adhesive precursors described herein, whether reactive adhesive precursors or initiated adhesive precursors, may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"), poly(vinyl pyrrolidinone) ("PVP"), poly(amino acids), poly(saccharides), such as dextran, chitosan, alginates, carboxymethylcellulose, oxidized cellulose, hydroxyethylcellulose and/or hydroxymethylcellulose, hyaluronic acid, and proteins such as albumin, collagen, casein, and gelatin. In embodiments, combinations of the foregoing polymeric materials may be utilized to form a core molecule. The polyethers, and more particularly poly(oxyalkylenes) or poly(ethylene glycol) or polyethylene glycol ("PEG"), may be utilized in some embodiments.

When the core molecule is small in molecular nature, any of a variety of hydrophilic functionalities may be used to make the first and second precursors water soluble. In embodiments, functional groups like hydroxyl, amine, sulfonate and carboxylate, may contribute to the water-solubility of a precursor. For example, the N-hydroxysuccinimide ("NHS") ester of subaric acid is insoluble in water, but by adding a sulfonate group to the succinimide ring, the NHS ester of subaric acid may be made water soluble, without affecting its ability to be used as a reactive group due to its reactivity towards amine groups.

In embodiments, an adhesive may be formed from reactive adhesive precursors through covalent, ionic, or hydrophobic bonds. Physical (non-covalent) crosslinks may result from complexation, hydrogen bonding, desolvation, Van der Waals interactions, ionic bonding, combinations thereof, and the like, and may be initiated by mixing two adhesive precursors that are physically separated until combined in situ or as a consequence of a prevalent condition in the physiological environment, including temperature, pH, ionic strength, combinations thereof, and the like. Chemical (covalent) crosslinking may be accomplished by any of a number of mechanisms including, but not limited to, free radical polymerization, condensation polymerization, anionic or cationic polymerization, step growth polymerization, electrophile-nucleophile reactions, combinations thereof, and the like.

In embodiments, the reactive adhesive precursor may be formed from a single type of reactive precursor or multiple types of reactive precursors. In other embodiments, where the adhesive is formed from multiple types of reactive adhesive precursors, for example two reactive adhesive precursors, the reactive adhesive precursors may be referred to as a first and second reactive adhesive precursor. Where more than one reactive adhesive precursor is utilized, in embodiments, at least one of the first and second adhesive precursors may be a crosslinker, and at least one other reactive adhesive precursor may be a macromolecule, and may be referred to herein as a "functional polymer".

In some embodiments, reactive adhesive precursors may include biocompatible multi-precursor systems that spontaneously crosslink when the adhesive precursors are mixed, but wherein the two or more adhesive precursors are individually stable prior to implantation. When the reactive adhesive precursors are mixed in an environment that permits reaction (e.g., as relating to pH, temperature, or solvent), the functional groups may react with each other to form covalent bonds. Reactive adhesive precursors become crosslinked when at least some of the reactive adhesive precursors can react with more than one other reactive adhesive precursor. For instance, an adhesive precursor with two functional groups of a first type may be reacted with a crosslinking adhesive precursor that has at least three functional groups of a second type capable of reacting with the first type of functional groups.

Such reactive components include, for example, first reactive adhesive precursors possessing electrophilic groups and second reactive adhesive precursors possessing nucleophilic groups. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first reactive adhesive precursor may react with a second set of nucleophilic functional groups on a second reactive adhesive precursor. In embodiments, such systems include a first reactive precursor including di- or multifunctional alkylene oxide containing moieties, and a second reactive precursor including macromers that are di- or multifunctional amines.

In embodiments the first and second adhesive precursors may be multifunctional, meaning that they may include two or more electrophilic or nucleophilic functional groups, such that, for example, an electrophilic functional group on the first reactive adhesive precursor may react with a nucleophilic functional group on the second reactive adhesive precursor to form a covalent bond and attach the filament to tissue. At least one of the first or second adhesive precursors includes more than two functional groups, so that, as a result of electrophilic-nucleophilic reactions, the adhesive precursors combine to form crosslinked polymeric products.

In embodiments, each of the first and second adhesive precursors may include only one category of functional groups, either only nucleophilic groups or only electrophilic functional groups, so long as both nucleophilic and electrophilic reactive adhesive precursors are used in the crosslinking reaction. Thus, for example, if the first reactive adhesive precursor has electrophilic functional groups such as N-hydroxysuccinimides, the second reactive adhesive precursor may have nucleophilic functional groups such as amines. On the other hand, if the first reactive adhesive precursor has electrophilic functional groups such as sulfosuccinimides, then the second reactive adhesive precursor may have nucleophilic functional groups such as amines or thiols.

In embodiments, a multifunctional electrophilic polymer such as a multi-arm PEG functionalized with multiple NHS groups may be used as a first reactive adhesive precursor and a multifunctional nucleophilic polymer such as trilysine may be used as a second reactive adhesive precursor. The multi-arm PEG functionalized with multiple NHS groups may, for example, have four, six or eight arms and a molecular weight of from about 5,000 to about 25,000. Other examples of suitable first and second precursors are described in U.S. Pat. Nos. 6,152,943, 6,165,201, 6,179,862, 6,514,534, 6,566,406, 6,605,294, 6,673,093, 6,703,047, 6,818,018, 7,009,034, and 7,347,850, the entire disclosures of each of which are incorporated by reference herein.

Synthetic materials that are readily sterilized and avoid the dangers of disease transmission that may accompany the use of natural materials may also be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200, 5,874,500, 5,543,441, 5,514,379, 5,410,016, 5,162,430, 5,324,775, 5,752,974, and 5,550,187.

In embodiments, the first and second adhesive precursors may represent two-part adhesives. In some embodiments, examples may include first and second adhesive precursors such as glues including albumin and glutaraldehyde materials, clotting agents such as fibrinogen and thrombin materials, and/or gelatin and thrombin materials. It is envisioned that these materials may be used in combination as a first and second adhesive precursor in any of the filaments described herein.

In some embodiments, the first adhesive precursor may be a functional polymer which includes pendant isocyanate groups. In some embodiments, the first adhesive precursor which includes isocyanates may react with the amine groups found naturally in tissue to form an adhesive. In some embodiments, the isocyanate precursors may be combined with second adhesive precursors which include pendant amine or hydroxyl groups, such as albumin, trilysine and/or polyethylene glycol, to form the adhesive.

The reaction conditions for forming crosslinked adhesives from first and second adhesive precursors may depend on the nature of the reactive adhesive precursor used as well as the surrounding environment. For example, in embodiments, the first and second adhesive precursors may be stable and/or non-reactive at a given pH and/or temperature, as the precursors are positioned within a biodegradable polymer forming the inner core of the filament body, but become reactive upon exposure to the pH and/or temperature of the tissue.

In embodiments, buffers may be added to the filaments and/or adhesive precursors described herein to assist with certain reactions. Buffers include, for example, sodium borate buffer (pH 10) and triethanol amine buffer (pH 7). In some embodiments, organic solvents such as ethanol or isopropanol may be added to improve the reaction speed of the first and second precursors.

In some embodiments, the first and second adhesive precursors may include functional polymers which include pendant click-reactive members. More specifically, in some embodiments, the first adhesive precursor may include a first click-reactive member and the second adhesive precursor may include a second click-reactive member complementary to the first click-reactive member. The term "click-reactive members" as used herein is intended to include those reactive members used in the processes known to those skilled in the art as Click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkly/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

a)

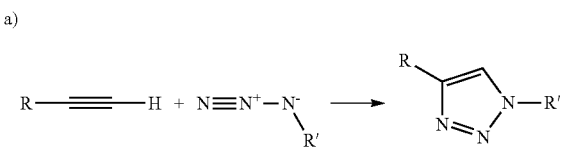

where R and R' represent the first and second portions of the suture surface.

The Diels-Alder reaction combines a diene (a molecule with two alternating double bonds) and a dienophile (an alkene) to make rings and bicyclic compounds. Examples include:

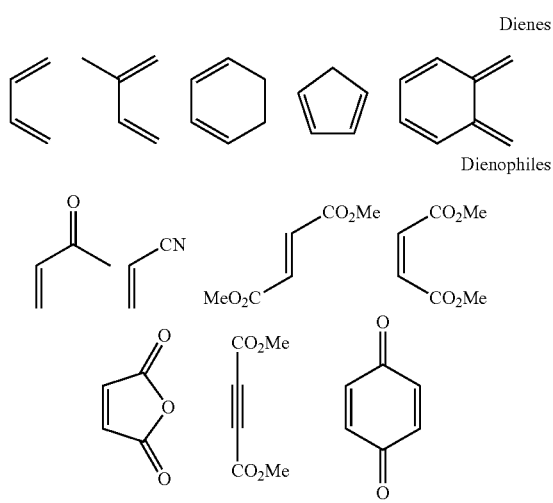

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

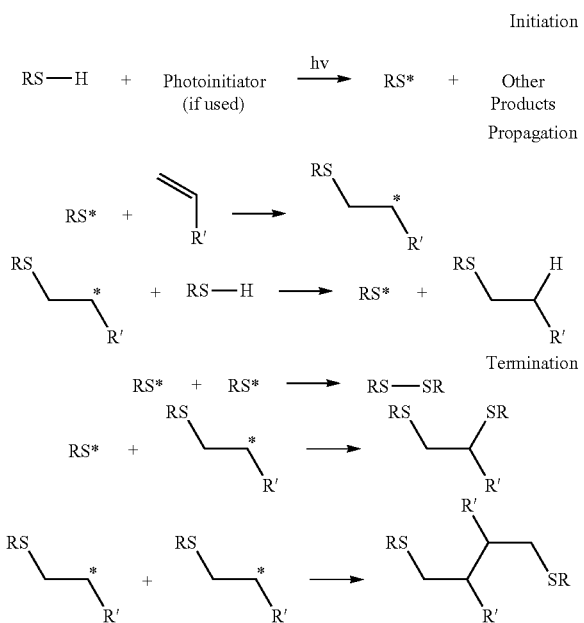

In embodiments, a first adhesive precursor and a second adhesive precursor are functionalized to include a first click-reactive member which includes at least one alkyne and a second click-reactive member which includes at least one azide, respectively. In embodiments, a first adhesive precursor and a second adhesive precursor are functionalized to include a first click-reactive member which includes at least one azide group and a second click-reactive member which includes at least one alkyne, respectively.

The first and second click-reactive members are intended to react and covalently bond the first and second precursors and attach the filament to tissue at a physiologic pH. However, in some embodiments, the first and second click-reactive members may react quicker or more completely following the addition of a catalyst, such as a pH modifier, a metal ion catalyst or the introduction of heat or radiation. In embodiments, the addition of UV radiation may enhance the formation of a covalent bond between the first and second click-reactive members. In embodiments, the addition of a metal catalyst, e.g., transition metal ions such as copper ions may assist with the formation of a covalent bond between the first and second click-reactive members.

In certain embodiments, the filaments described herein may include: an inner core which includes a first adhesive precursor including a first click reactive member, e.g., azide(s) and a reducing agent such as ascorbic acid; and, an outer core including a dry coating which includes a second adhesive precursor having a second complementary click reactive member, e.g., alkyne(s) and a catalyst such as a metal ion catalyst, i.e., Copper and/or Cu(II). Upon wetting of the filament, the reducing agent, in this embodiment ascorbic acid, may leach out of the core via the access created by the formation of the barb to a depth sufficient to expose a portion of the inner core and mix with the materials of the outer sheath. The combination of the reducing agent with Cu(II), will reduce Cu(II) to Cu(I) which may activate or catalyze a reaction between the first adhesive precursor functionalized with azides and the second adhesive precursor functionalized with alkynes. It is envisioned that reducing agents like ascorbic acid do not typically leach out of the inner core until aqueous fluids are present, in that ambient moisture is not enough to activate such a reaction, thereby enhancing the stability of such a filament prior to use.

The adhesive precursor(s) may be combined with the filaments described herein using any suitable method within the purview of one skilled in the art. In embodiments, the adhesive precursor may be a solid, such as powder, particle, fiber, bead, microbead and the like, which may be combined with any of the polymeric materials described herein to form the inner core and/or outer sheath of the filament. In some embodiments, it is envisioned that upon degradation of the inner core or outer sheath, the adhesive precursors may be released and/or leach from the filament and transition from non-adherent to adherent.

In embodiments, the adhesive precursor and the polymeric material may be mixed to form a blend of materials. The blend may be further processed, e.g., extruded, coated, molded, etc., to form the inner core, outer sheath and/or both.

Filaments and/or sutures in accordance with the present disclosure may optionally be coated or impregnated with one or more medico-surgically useful substances, e.g., bioactive agents which accelerate or beneficially modify the healing process when the filament is applied to a wound or surgical site. Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial to the patient and tend to promote the healing process. For example, a filament can be provided with a bioactive agent that may be deposited at the site of implantation. The bioactive agent can be chosen for its antimicrobial properties, capability for promoting wound repair and/or tissue growth, or for specific indications such as thrombosis. In embodiments, combinations of such agents may be applied to a filament of the present disclosure.

The term "antimicrobial agent" as used herein includes an agent, which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines like minocycline, fusidic acid, trimethoprim, metronidazole, a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of antiseptics and disinfectants which may be utilized as the antimicrobial agent include hexachlorophene; cationic biguanides like chlorhexidine and cyclohexidine; iodine and iodophores like povidone-iodine; ionic silver, ionic silver glasses, halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some useful embodiments, at least one of the antimicrobial agents may be an antiseptic such as triclosan.

To promote wound repair and/or tissue growth, one or more bioactive agents known to achieve either or both of these objectives can also be applied to the filament as wound repair agents or tissue growth agents. Such clotting or "fibrosis-inducing agents" are utilized for the promotion of aneurysm or embolism when it is desired for treatment of particular vascular insults or diseases, or for example, blocking a tumor from its primary blood supply.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, monoclonal antibody and polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly (ethylene glycol)-methylated collagen, an inflammatory cytokine, TGF-β, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs (L-azetidine-2-carboxylic acid (LACA), cishydroxyproline, d,L-3,4-dehydroproline, Thiaproline, α-dipyridyl, β-aminopropionitrile fumarate); MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α-2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Filaments in accordance with this disclosure can also include, for example, biologically acceptable plasticizers, antioxidants, dyes, and pigments, which can be impregnated into the filament(s) utilized to form a suture of the present disclosure or included in a coating thereon.

In embodiments, filaments of the present disclosure may be dyed in order to increase the visibility of the filament in the surgical field. Any dye suitable for incorporation in implantable filaments can be used. Such dyes include, but are not limited to, carbon black, bone black, D&C Green No. 6, and D&C Violet No. 2. In embodiments, filaments in accordance with the present disclosure may be dyed by adding dye in an amount up to about a few percent, in other embodiments by adding dye in an amount of about 0.2%, in still further embodiments in an amount from about 0.06% to about 0.08%.

As noted above, bioactive agents may be impregnated into the materials utilized to form filaments of the present disclosure or deposited on the surface thereof. Bioactive agents may be applied onto a barbed filament of the present disclosure utilizing any method within the purview of one skilled in the art including, for example, dipping, spraying, vapor deposition, brushing, compounding and the like.

Figure 6:
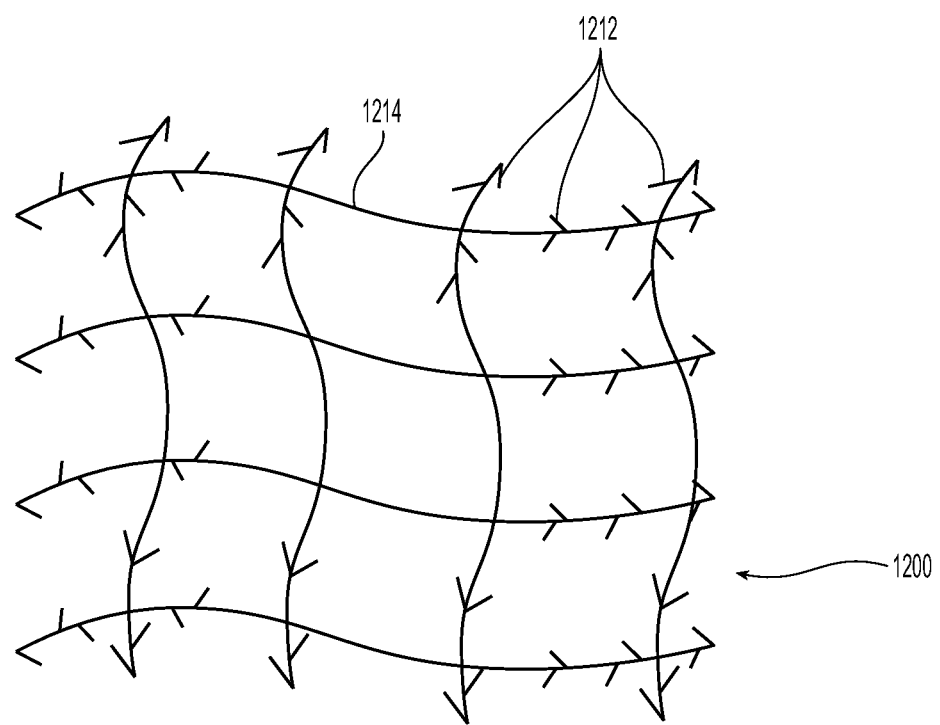

In embodiments the filaments described herein may be used to form other fibrous implants, such as a surgical mesh, a vaso-occlusive device, a suture pledget, a staple buttress and the like. For example, as illustrated in FIG. 6, a surgical mesh 1200 made from at least one filament 1214 including a plurality of barbs 1212 as described herein. Filament 1214 includes an inner core and an outer sheath which include at least one adhesive precursor. It is envisioned that the surgical mesh of FIG. 6 will become adherent following implantation and the adhesive precursor transitions from a non-adherent state to an adherent state thereby anchoring the surgical mesh to the tissue via the inner core portions located near the barbs of the filaments.

Once the filaments are constructed, they can be sterilized and packaged by any means within the purview of those skilled in the art with or without a needle.

In embodiments, methods of forming a barbed suture are also described which include: providing a filament having an elongate body and including an inner core and an outer sheath, the inner core including at least one adhesive precursor; and, forming a plurality of barbs on a surface of the filament which expose a portion of the inner core including the adhesive precursor to allow the inner core to adhere to tissue following implantation.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical suture comprising:
 a filament having an elongated body including an inner core and outer sheath, the inner core including a first adhesive precursor and the outer sheath including at least one of a second adhesive precursor or a catalyst, and
 a plurality of barbs formed along a surface of the elongated body and exposing a portion of the inner core and the first adhesive precursor and the outer sheath and at least one of the second adhesive precursor or the catalyst.

2. The surgical suture of claim 1 wherein the adhesive precursor comprises a cyanoacrylate.

3. The surgical suture of claim 1 wherein the inner core further comprises a bioabsorbable polymer.

4. The surgical suture of claim 1 wherein the outer sheath further comprises a bioabsorbable polymer.

5. The surgical suture of claim 1 wherein the plurality of barbs are arranged in a bidirectional manner.

6. The surgical suture of claim 1 wherein at least one end of the filament is attached to a needle.

7. The surgical suture of claim 1 wherein the first and second adhesive precursor comprises a two-part adhesive when combined.

8. The surgical suture of claim 1 wherein a barb of the plurality of barbs is a compound barb including at least a first and second barb inner surface.

9. The surgical suture of claim 8 wherein the first barb inner surface comprises the inner core material.

10. The surgical suture of claim 9 wherein the second barb inner surface comprises the inner core material.

11. The surgical suture of claim 8, wherein the compound barb further includes at least a first and second inner body surfaces, wherein first inner body surface penetrates through the outer sheath to expose the inner core without penetrating the inner core and the second inner body surface runs along a length of the exposed inner core.

12. The surgical suture of claim 11, wherein the first body inner surface, the first barb inner surface and the second barb inner surface include only the outer sheath including the second precursor adhesive or catalyst and the second inner body surface includes only inner core and the first adhesive precursor.

13. The surgical suture of claim 1 further comprising a second inner core comprising at least one of a second adhesive precursor or a catalyst.

14. The surgical suture of claim 1 wherein the first and second adhesive precursors comprises reactive adhesive precursors.

15. The surgical suture of claim 1 wherein the first and second adhesive precursors comprises initiated adhesive precursors.

16. The surgical suture of claim 1 wherein the first and second adhesive precursors comprises click reactive members.

17. The surgical suture of claim 1 wherein the first adhesive precursor comprises a first material including pendant electrophilic groups and the second adhesive precursor comprises a second material including pendant nucleophilic groups capable of reacting with the electrophilic groups of the first adhesive precursor.

18. A method of forming a barbed suture comprising:
providing a filament having an elongate body and including an inner core and an outer sheath, the inner core including at least one first adhesive precursor and the outer sheath including at least one of a second adhesive precursor or a catalyst; and,
forming a plurality of barbs on a surface of the filament which expose a portion of the inner core including the first adhesive precursor and the outer sheath including at least one of the second adhesive precursor or the catalyst to allow the inner core to adhere to tissue following implantation.

19. A surgical mesh comprising:
at least one filament having an elongated body including an inner core and outer sheath, the inner core including a first adhesive precursor and the outer sheath including at least one of a second adhesive precursor or a catalyst, and,
a plurality of barbs formed along a surface of the elongated body and exposing a portion of the inner core and the first adhesive precursor and the outer sheath and at least one of the second adhesive precursor or the catalyst.

\* \* \* \* \*